United States Patent
Guan et al.

(10) Patent No.: US 11,440,989 B2
(45) Date of Patent: Sep. 13, 2022

(54) APPLICATION OF MANNICH BASE IN FLAME-RETARDANT POLYURETHANE MATERIAL

(71) Applicants: Jiahua Science & Technology Development (Shanghai) Ltd., Shanghai (CN); Jiahua Chemicals Inc., Fushun (CN)

(72) Inventors: Yongjian Guan, Fushun (CN); Ping Li, Fushun (CN); Zhijun Li, Fushun (CN); Feng Wang, Fushun (CN); Yubo Li, Fushun (CN)

(73) Assignees: Jiahua Science & Technology Development (Shanghai) Ltd., Shanghai (CN); Jiahua Chemicals Inc., Fushun (CN)

( * ) Notice: Subject to any disclaimer, the term of this patent is extended or adjusted under 35 U.S.C. 154(b) by 315 days.

(21) Appl. No.: 16/685,953

(22) Filed: Nov. 15, 2019

(65) Prior Publication Data

US 2020/0283562 A1 Sep. 10, 2020

(30) Foreign Application Priority Data

Sep. 17, 2018 (CN) .......................... 201811082504.7

(51) Int. Cl.
| | |
|---|---|
| *C08G 18/48* | (2006.01) |
| *C09K 21/14* | (2006.01) |
| *C08G 18/38* | (2006.01) |
| *C08G 18/70* | (2006.01) |
| *C07C 213/02* | (2006.01) |
| *C07C 215/28* | (2006.01) |
| *C08G 18/50* | (2006.01) |
| *C08G 65/26* | (2006.01) |
| *C07C 215/50* | (2006.01) |
| *C08J 9/04* | (2006.01) |

(52) U.S. Cl.
CPC ........ *C08G 18/4879* (2013.01); *C07C 213/02* (2013.01); *C07C 215/28* (2013.01); *C07C 215/50* (2013.01); *C08G 18/381* (2013.01); *C08G 18/482* (2013.01); *C08G 18/4829* (2013.01); *C08G 18/5066* (2013.01); *C08G 18/70* (2013.01); *C08G 65/2639* (2013.01); *C08G 65/2648* (2013.01); *C08J 9/04* (2013.01); *C09K 21/14* (2013.01); *C08G 2110/005* (2021.01); *C08J 2375/08* (2013.01)

(58) Field of Classification Search
CPC .......... C08G 18/4879; C08G 2110/005; C08G 18/381; C08G 18/4829; C08G 18/70; C08G 18/482; C08G 18/5066; C08G 65/2639; C08G 65/2648; C09K 21/14; C07C 213/02; C07C 215/28; C07C 215/50; C08J 9/04; C08J 2375/08
See application file for complete search history.

(56) References Cited

U.S. PATENT DOCUMENTS 4,797,429 A * 1/1989 Thorpe .............. C08G 18/5033
521/163

FOREIGN PATENT DOCUMENTS

| CN | 103073986 A | 5/2013 |
|---|---|---|
| CN | 103539932 A * | 1/2014 |
| CN | 107556448 A | 1/2018 |

OTHER PUBLICATIONS

First Office Action in corresponding CN Patent Application 201811082504.7, dated Jun. 30, 2020, and English Translation thereof, 22 total pages.
Xu et al. "Synthesis and application of Mannich polyether polyol" Thermosetting Resin, vol. 30, No. 6, Nov. 2015, and English Translation thereof, 15 total pages.
Zhang, "Study on the Preparation of New Flame Retardant Polyether Polyol" Thermosetting Resin, vol. 17, No. 6, Nov. 2002, and English Translation thereof, 10 total pages.

* cited by examiner

*Primary Examiner* — Rabon A Sergent
(74) *Attorney, Agent, or Firm* — Armstrong Teasdale LLP

(57) ABSTRACT

Application of a Mannich base in a flame-retardant polyurethane material is provided. The Mannich base has a structure represented by a formula (I). In the Mannich base, flame-retardant groups, i.e., halogens are introduced at the second, fourth and sixth positions of a phenyl group, and flame-retardant elements, i.e., halogens and nitrogen are introduced into synthesized polyether polyol, giving the synthesized polyether polyol good flame retardance. The amount of active hydrogen in the Mannich base is small so that occurrence of side reactions during the synthesis of the polyether polyol is reduced, and the viscosity of the flame-retardant polyether polyol is lowered. Due to autocatalytic performance of tertiary amido in the flame-retardant polyether polyol, use of a catalyst can be reduced and even avoided during the synthesis. A preparation method of the Mannich base is also provided.

12 Claims, No Drawings

APPLICATION OF MANNICH BASE IN FLAME-RETARDANT POLYURETHANE MATERIAL

CROSS-REFERENCE TO RELATED APPLICATION

This application claims priority benefits to Chinese Patent Application No. 201811082504.7, filed on Sep. 17, 2018. The contents of all of the aforementioned applications are incorporated herein by reference.

TECHNICAL FIELD

The present disclosure belongs to the technical field of organic molecular materials and particularly relates to application of a Mannich base in a flame-retardant polyurethane material.

BACKGROUND

A Mannich reaction is also called an aminomethylation reaction, is an organic chemical reaction for producing a β-amino (carbonyl) compound through subjecting an active hydrogen-containing compound (generally, a carbonyl compound) to condensation with formaldehyde and amine (secondary amine, tertiary amine or ammonia) and is extensively applied to the synthesis of nitrogen-containing molecules, particularly secondary amine and tertiary amine derivatives; and this reaction has extensive application in synthesis of medicines and alkaloids, particularly in recent years, the application of this reaction in synthesis of explosives, propellants, etc. has attracted great attention of chemists.

The product β-amino (carbonyl) compound of the Mannich reaction is called a Mannich base, i.e., Mannich bases for short. The Mannich bases comprise an organic ketone Mannich base, an aldehyde Mannich base, a carboxylic acid Mannich base and an aryl phenol Mannich base, which are prepared through subjecting organic ketone, aldehyde, carboxylic acid and aryl phenol as acid components to reactions with aldehyde and amine, and corresponding Mannich bases produced through carrying out reactions by taking alkynes, quinone, a heterocyclic compound, indole, guanidine salts, benzamide, phenoxy oxolinic acid, etc. as acid components.

The Mannich bases and derivatives thereof are initially applied as drugs, products of the reaction start to continuously go deep into various fields of production of means of living of human as time goes on, for example, the products can be applied to synthesis of sedatives-analgesics, bactericides, hydrops depressants, antineoplastic drugs, liver protecting drugs, anticoagulants, etc. in the aspect of medicines; as corrosion inhibitors, the Mannich bases are relatively good in effect and can serve as anti-rust agents of iron and steel in seawater, acid corrosion inhibitors of internal walls of petroleum product reservoirs, various pickling corrosion inhibitors, etc.; in addition, the Mannich bases are abundant in products and applications in the aspects of explosives and propellants, polymeric flocculants, vulcanization accelerators, herbicides, dispersants, antioxidants, reactive dyes, food flavorings and metal chelants.

SUMMARY

Therefore, a technical problem to be solved by the present disclosure is to provide new application of a Mannich base in a flame-retardant polyurethane material.

Thereby, the present disclosure provides a technical solution as follows:

The present disclosure provides application of a Mannich base in a flame-retardant polyurethane material. The Mannich base has a structure represented by a formula (I).

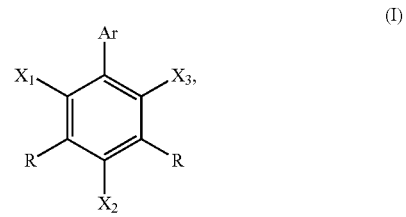

wherein, Ar is hydroxyl or hydroxyl substituted C1~C16 alkyl, R is

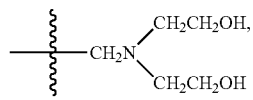

and $X_1$, $X_2$ and $X_3$, independently of each other, represent a halogen.

Optionally, in the above-mentioned application, $X_1$, $X_2$ and $X_3$, independently of each other, represent bromo or chloro.

Optionally, in the above-mentioned application, the Mannich base has a structure represented by a formula (II):

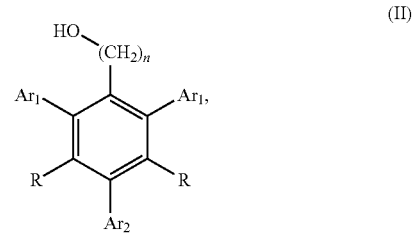

wherein, n is an integer of 1-16, R is

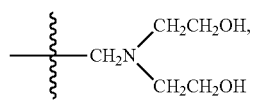

and $Ar_1$ and $Ar_2$, independently of each other, represent bromo or chloro.

Optionally, in the above-mentioned application, the Mannich base has a structure represented by any of the following formulae (I-1)-(I-12):

(I-1) 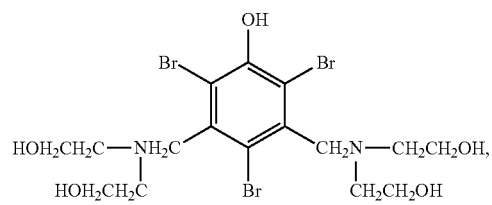
(I-2) 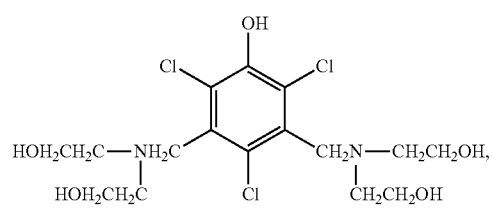
(I-3) 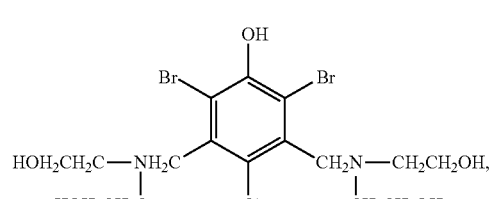
(I-4) 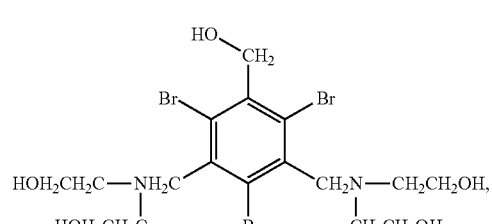
(I-5) 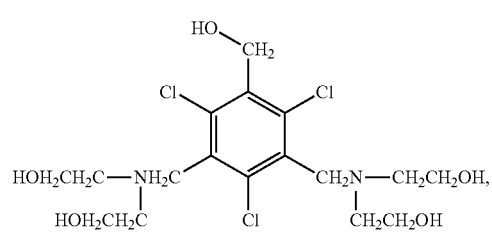
(I-6) 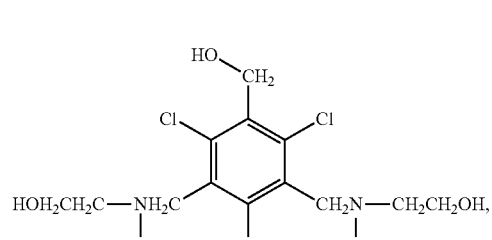
(I-7) 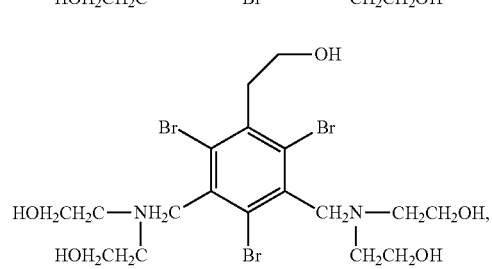
(I-8) 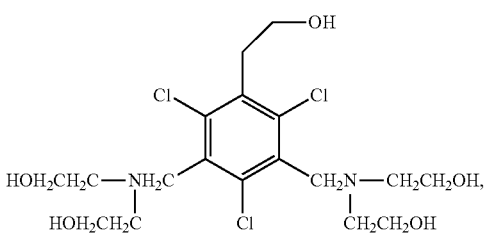
(I-9) 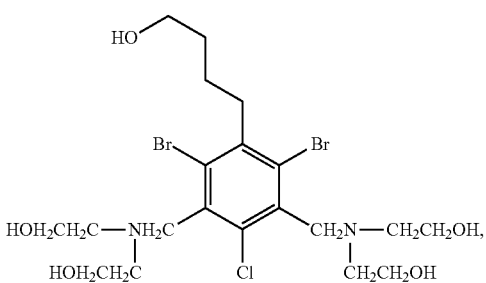
(I-10) 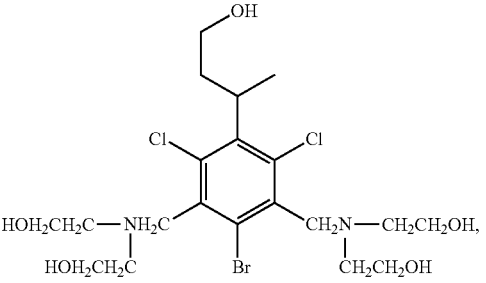
(I-11) 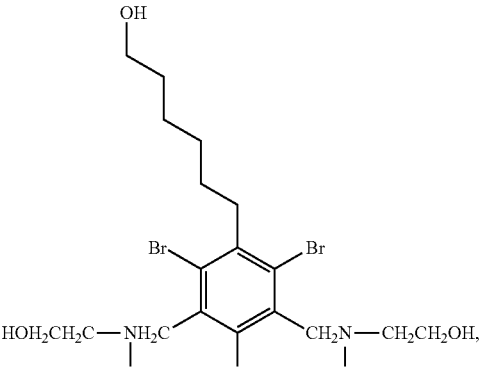
(I-12) 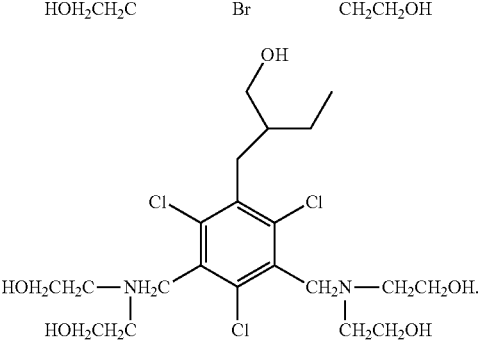
Optionally, in the above-mentioned application, the Mannich base is prepared by a method including the following steps:
(1) performing a reaction by heating diethanolamine, then adding paraformaldehyde into the diethanolamine in batches, and controlling a temperature of 50-60° C., producing 3-hydroxyethyl-1,3-oxazolidine; and (2) performing a reaction by adding a phenyl compound into the 3-hydroxyethyl-1,3-oxazolidine, producing the Mannich base with a structure represented by the formula (I);

wherein the phenyl compound has a structure represented by a formula (I') as follows:

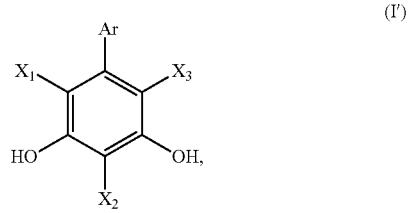

wherein, Ar is hydroxyl or hydroxyl substituted C1~C16 alkyl, R is

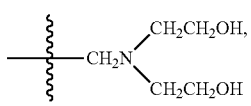

and $X_1$, $X_2$ and $X_3$, independently of each other, represent a halogen.

Further optionally, in the above-mentioned application, the step (1) further includes the step of dewatering the produced 3-hydroxyethyl-1,3-oxazolidine to enable the 3-hydroxyethyl-1,3-oxazolidine has a moisture content of equal to or less than 0.5%.

Optionally, in the above-mentioned application, in the step (2), the 3-hydroxyethyl-1,3-oxazolidine is reacted with the phenyl compound at a temperature of 80-85° C. for a period of 2.5-3 h.

Optionally, in the above-mentioned application, a mole ratio of the diethanolamine to the paraformaldehyde to the phenyl compound is (2-2.15):(2-2.1):1.

Optionally, in the above-mentioned application, the paraformaldehyde is added in 4 batches within a period of not exceeding 40 minutes under a temperature of 50-60° C.

Optionally, in the above-mentioned application, the phenyl compound is added in 3-4 batches within a period of not exceeding 2 hours.

Compared with the prior art, the present disclosure has the following advantages:

1. According to the application of the Mannich base in the flame-retardant polyurethane material, provided by the present disclosure, the Mannich base has a structure represented by the formula (I).

In the Mannich base with the structure represented by the formula (I), flame-retardant groups, i.e., halogens are introduced at the second, fourth and sixth positions of a phenyl group. In the structure represented by the formula (I), Ar is hydroxyl or hydroxyl substituted C1~C16 alkyl, an Ar group and/or an R group provide/provides active hydrogen atoms, and thus, the above-mentioned Mannich base can serve as an initiator and copolymerize with an epoxide to synthesize a polyether polyol; and flame-retardant elements, i.e., halogens and nitrogen are introduced into the synthesized polyether polyol, so that the synthesized polyether polyol has good flame retardance.

The synthesized flame-retardant polyether polyol can serve as an industrial raw material of polyurethane and react with an isocyanate to form a urethane bond and a urea bond, flame-retardant groups are introduced into a principal chain of a polyurethane material, the polyurethane material is subjected to soft-segment flame-retardant modification, and the Mannich base with the structure represented by the formula (I) has flame-retardant groups of a high ratio and serve as an initiating raw material, so that the final obtained flame-retardant polyurethane material has flame-retardant elements of high content, and the limiting oxygen index (LOI) of the polyurethane material is remarkably increased. The flame-retardant polyurethane material is a reactive flame-retardant material obtained through introducing the flame-retardant groups into the principal chain, so that the influence on mechanical properties of the polyurethane material is relatively low, the polyurethane material can have both flame retardance and mechanical properties, and great lowering of mechanical properties such as cracking, powdering or compressive deformation is avoided.

Meanwhile, R in the Mannich base is

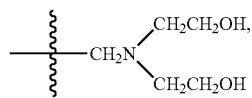

a tertiary amine structure is introduced into the synthesized flame-retardant polyether polyol, and tertiary amine catalysts are catalysts with high performance employed during synthesis of the polyurethane material. The polyether polyol synthesized by the Mannich base with the structure represented by the formula (I) has high flame retardance, and meanwhile, tertiary amido of the Mannich base can catalyze a polymerization reaction between the polyether polyol and an isocyanate, so that the amount of the catalyst required to be used during the synthesis of the polyurethane material is effectively reduced, even, the use of the catalyst is avoided, then, biological toxicity and environmental toxicity during the synthesis of the polyurethane material are lowered, and the environment friendliness of the polyurethane material is improved.

On the other hand, in the Mannich base, halogens are symmetrically introduced at the second, fourth and sixth positions of a phenyl group, active hydrogen on the phenyl group is reduced, the occurrence of side reactions when the Mannich base is applied to the synthesis of substances such as the polyether polyol is effectively reduced, then, dimers or polymers resulting from the side reactions are reduced, the viscosity of the synthesized flame-retardant polyether polyol is lowered, and the problems that all ingredients are non-uniform in mixing during the foaming of a polyurethane material due to too high system viscosity and the fluidity of material fluid is poor are avoided.

Therefore, according to new application of the Mannich base with a structure represented by the formula (I) in a flame-retardant polyurethane material, provided by the present disclosure, the improvement on flame retardance of the polyurethane material is facilitated, the limiting oxygen index of the polyurethane material is increased, the use safety of the polyurethane material in the fields of architecture, traffic, etc. is improved, and the requirements on high flame retardant rating are met; reaction byproducts during synthesis of substances such as polyether polyol by the Mannich base can be reduced, and the viscosity of products is lowered; and the use of a catalyst required during synthesis of the polyurethane material is reduced and even avoided, the synthesis cost of the polyurethane material is reduced, and the environment friendliness of the polyurethane material is improved.

2. The preparation method of the Mannich base, provided by the present disclosure, includes the steps: firstly, adding paraformaldehyde into diethanolamine in batches, and controlling a temperature to be 50-60° C., producing 3-hydroxyethyl-1,3-oxazolidine; and performing a reaction by adding a phenyl compound into the 3-hydroxyethyl-1,3-oxazolidine, producing the Mannich base with a structure represented by the formula (I).

The diethanolamine is of a liquid state during the reaction, and the diethanolamine can uniformly and stably react with the paraformaldehyde to produce the 3-hydroxyethyl-1,3-oxazolidine. The paraformaldehyde has good reactivity, efficiently condenses with an amine and is added in batches, and thus, the uniformity of a reaction system is improved, and too high viscosity of a product is avoided. The Mannich base, which has flame-retardant groups and catalytic groups and is suitable for producing low-viscosity polyether polyols, is produced through subjecting the produced 3-hydroxyethyl-1,3-oxazolidine to a reaction with the phenyl compound with a structure represented by the formula (I').

The preparation method of the Mannich base with the structure represented by the formula (I) is simple in steps and easy to realize in reaction conditions, thereby being applicable to large-scale industrial production.

3. The preparation method of the Mannich base, provided by the present disclosure, further includes the step of dewatering the produced 3-hydroxyethyl-1,3-oxazolidine to enable the 3-hydroxyethyl-1,3-oxazolidine has a moisture content of equal to or less than 0.5%, so that the moisture content of the synthesized Mannich base is effectively lowered, the consumption of epoxy monomers and increase of reaction byproducts caused by moisture in the Mannich base when polyether polyols are synthesized by using the Mannich base are avoided, and thus, the purity of the produced polyether polyols is improved, the difficulty of treatment of the produced polyether polyols is lowered, and a production process of the polyether polyols is simplified.

DETAILED DESCRIPTION

Implementation modes of the present disclosure are described below through specific embodiments, unless otherwise mentioned, experimentation methods disclosed in the present disclosure all employ the conventional technologies in this technical field, and reagents and raw materials employed in the embodiments all can be purchased on the market.

In the undermentioned embodiments, an isocyanate employed is polymethylenepolyphenyl polyisocyanate (PM200, Yantai Wanhua), a foam stabilizer is a foam stabilizer for hard foam (Momentive L-6900), a foamer is HCFC-14 1b (monofluorodichloroethane), a polyether polyol taking saccharose as an initiator is Puranol RF 4110 (Shanghai Jiahua), and a polyether polyol taking sorbitol as an initiator is Puranol RF 451 (Shanghai Jiahua).

Embodiment 1

The present embodiment provides a Mannich base with a structure represented by a formula (I-1) as follows:

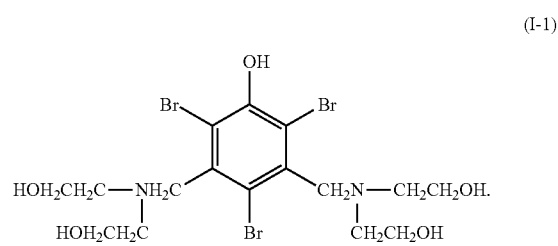

The Mannich base represented by the formula (I-1) is prepared through the following steps:

(1) adding 52.6 g of diethanolamine into a 250 mL round-bottomed flask, stirring, and heating up to a temperature of 40-45° C.; and then, adding 15 g of paraformaldehyde (molecular weight: 30) into the flask in four batches in a manner that the feeding time interval of each batch is 15 min and a temperature is controlled to be 50-55° C. during feeding of the paraformaldehyde;

After the paraformaldehyde is added completely, continuing to perform a reaction for a period of 3 h at a temperature of 50° C. to produce 3-hydroxyethyl-1,3-oxazolidine; and Heating up to a temperature of 100° C., and subjecting the produced 3-hydroxyethyl-1,3-oxazolidine to depressurized dewatering to enable the 3-hydroxyethyl-1,3-oxazolidine has a moisture content of equal to or less than 0.5%; and (2) cooling down to a temperature of 60-65° C., and adding 83 g of 2,4,6-tribromophenol (a phenyl compound represented by a formula (I'-1)) into the 3-hydroxyethyl-1, 3-oxazolidine in 2 h in 3-4 batches; and after adding is completed, continuing to perform a reaction for a period of 2.5 h at a temperature of 80° C., thereby preparing the Mannich base represented by the formula (I-1).

A reaction route is shown as follows:

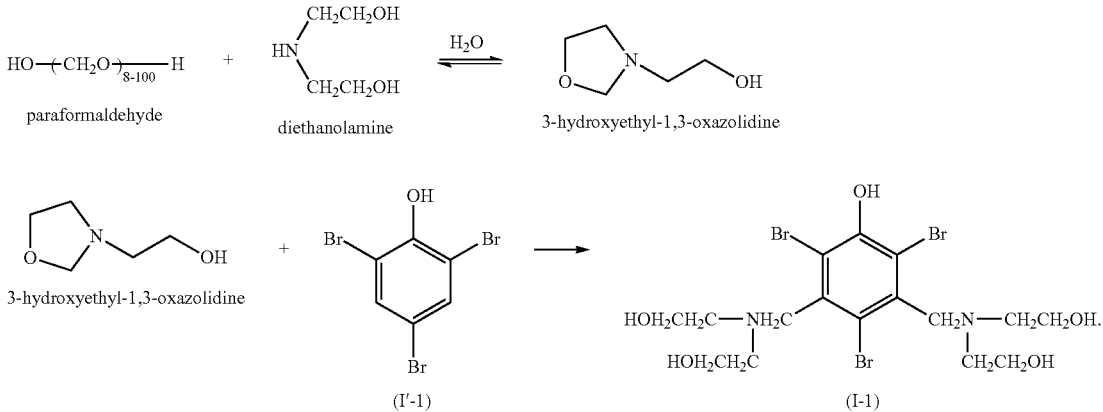

Embodiment 2

The present embodiment provides a Mannich base with a structure represented by a formula (I-2) as follows:

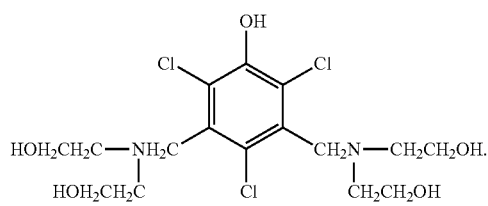

(I-2)

The Mannich base represented by the formula (I-2) is prepared through the following steps:

(1) adding 56.5 g of diethanolamine into a 250 mL round-bottomed flask, stirring, and heating up to a temperature of 40-45° C.; and then, adding 15 g of paraformaldehyde (molecular weight: 30) into the flask in four batches in a manner that the feeding time interval of each batch is 15 min and a temperature is controlled to be 55-60° C. during feeding of the paraformaldehyde;

After the paraformaldehyde is added completely, continuing to perform a reaction for a period of 3 h at a temperature of 55° C. to produce 3-hydroxyethyl-1,3-oxazolidine; and Heating up to a temperature of 100° C., and subjecting the produced 3-hydroxyethyl-1,3-oxazolidine to depressurized dewatering to enable the 3-hydroxyethyl-1,3-oxazolidine has a moisture content of equal to or less than 0.5%; and (2) cooling down to a temperature of 60-65° C., and adding 49.4 g of 2,4,6-trichlorophenol (a phenyl compound represented by a formula (I'-2)) into the 3-hydroxyethyl-1,3-oxazolidine in 2 h in 3-4 batches; and after adding is completed, continuing to perform a reaction for a period of 3 h at a temperature of 80° C., thereby preparing the Mannich base represented by the formula (I-2).

A reaction route is shown as follows:

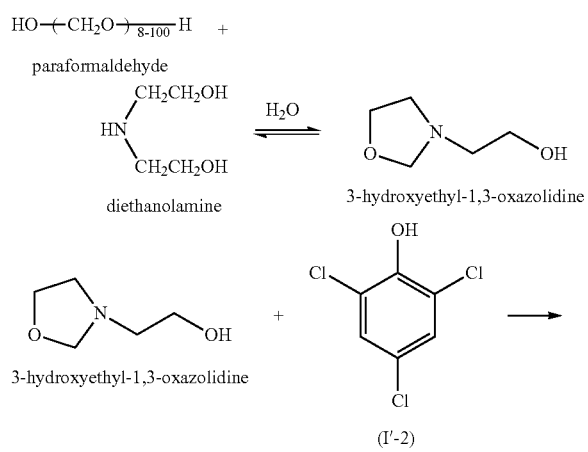

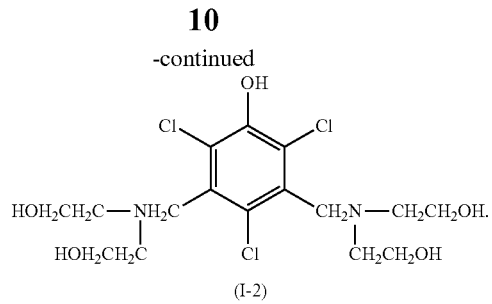

(I-2)

Embodiment 3

The present embodiment provides a Mannich base with a structure represented by a formula (I-3) as follows:

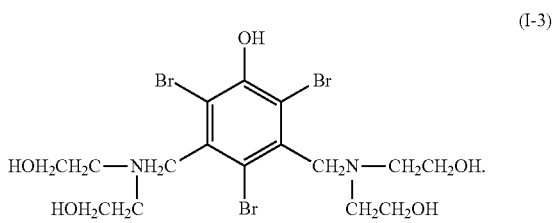

(I-3)

The Mannich base represented by the formula (I-3) is prepared through the following steps:

(1) adding 52.6 g of diethanolamine into a 250 mL round-bottomed flask, stirring, and heating up to a temperature of 40-45° C.; and then, adding 15.75 g of paraformaldehyde (molecular weight: 30) into the flask in four batches in a manner that the feeding time interval of each batch is 15 min and a temperature is controlled to be 50-55° C. during feeding of the paraformaldehyde;

After the paraformaldehyde is added completely, continuing to perform a reaction for a period of 3 h at a temperature of 55° C. to produce 3-hydroxyethyl-1,3-oxazolidine; and Heating up to a temperature of 100° C., and subjecting the produced 3-hydroxyethyl-1,3-oxazolidine to depressurized dewatering to enable the 3-hydroxyethyl-1,3-oxazolidine has a moisture content of equal to or less than 0.5%; and (2) cooling down to a temperature of 60-65° C., and adding 71.6 g of 2,6-dibromo-4-chlorophenol (a phenyl compound represented by a formula (I'-3)) into the 3-hydroxyethyl-1,3-oxazolidine in 2 h in 3-4 batches; and after adding is completed, continuing to perform a reaction for a period of 3 h at a temperature of 85° C., thereby preparing the Mannich base represented by the formula (I-3).

A reaction route is shown as follows:

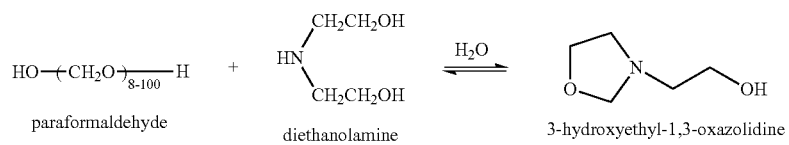

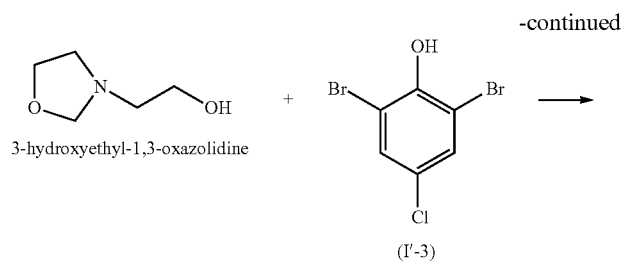
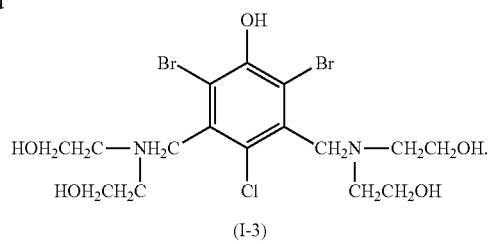

Embodiment 4

The present embodiment provides a Mannich base with a structure represented by a formula (I-4) as follows:

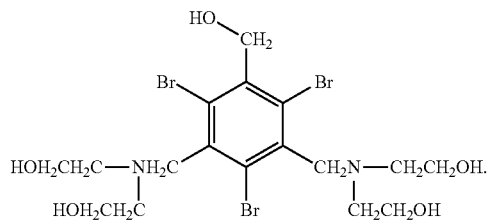

The Mannich base represented by the formula (I-4) is prepared through the following steps:

(1) adding 56.5 g of diethanolamine into a 250 mL round-bottomed flask, stirring, and heating up to a temperature of 40-45° C.; and then, adding 15.75 g of paraformaldehyde (molecular weight: 30) into the flask in four batches in a manner that the feeding time interval of each batch is 15 min and a temperature is controlled to be 55-60° C. during feeding of the paraformaldehyde;

After the paraformaldehyde is added completely, continuing to perform a reaction for a period of 3 h at a temperature of 60° C. to produce 3-hydroxyethyl-1,3-oxazolidine; and Heating up to a temperature of 100° C., and subjecting the produced 3-hydroxyethyl-1,3-oxazolidine to depressurized dewatering to enable the 3-hydroxyethyl-1,3-oxazolidine has a moisture content of equal to or less than 0.5%; and (2) cooling down to a temperature of 60-65° C., and adding 86.2 g of 2,4,6-tribromobenzalcohol (a phenyl compound represented by a formula (I'-4)) into the 3-hydroxyethyl-1,3-oxazolidine in 2 h in 3-4 batches; and after adding is completed, continuing to perform a reaction for a period of 2.5 h at a temperature of 80° C., thereby preparing the Mannich base represented by the formula (I-4).

A reaction route is shown as follows:

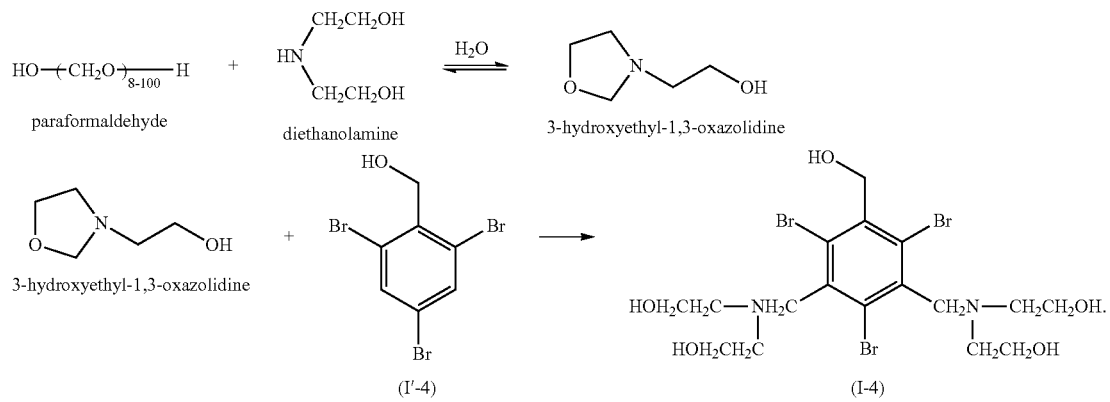

Embodiment 5

The present embodiment provides a Mannich base with a structure represented by a formula (I-5) as follows:

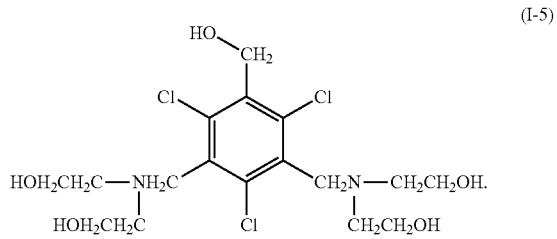

The Mannich base represented by the formula (I-5) is prepared through the following steps:

(1) adding 52.6 g of diethanolamine into a 250 mL round-bottomed flask, stirring, and heating up to a temperature of 40-45° C.; and then, adding 15 g of paraformaldehyde (molecular weight: 30) into the flask in four batches in a manner that the feeding time interval of each batch is 15 min and a temperature is controlled to be 50-55° C. during feeding of the paraformaldehyde;

After the paraformaldehyde is added completely, continuing to perform a reaction for a period of 3 h at a temperature of 55° C. to produce 3-hydroxyethyl-1,3-oxazolidine; and Heating up to a temperature of 100° C., and subjecting the produced 3-hydroxyethyl-1,3-oxazolidine to depressurized dewatering to enable the 3-hydroxyethyl-1,3-oxazolidine has a moisture content of equal to or less than 0.5%; and (2) cooling down to a temperature of 60-65° C., and adding 52.9 g of 2,4,6-trichlorobenzalcohol (a phenyl compound represented by a formula (I'-5)) into the 3-hydroxyethyl-1,3-oxazolidine in 2 h in 3-4 batches; and after adding is completed, continuing to perform a reaction for a period of 2.5 h at a temperature of 85° C., thereby preparing the Mannich base represented by the formula (I-5).

A reaction route is shown as follows:

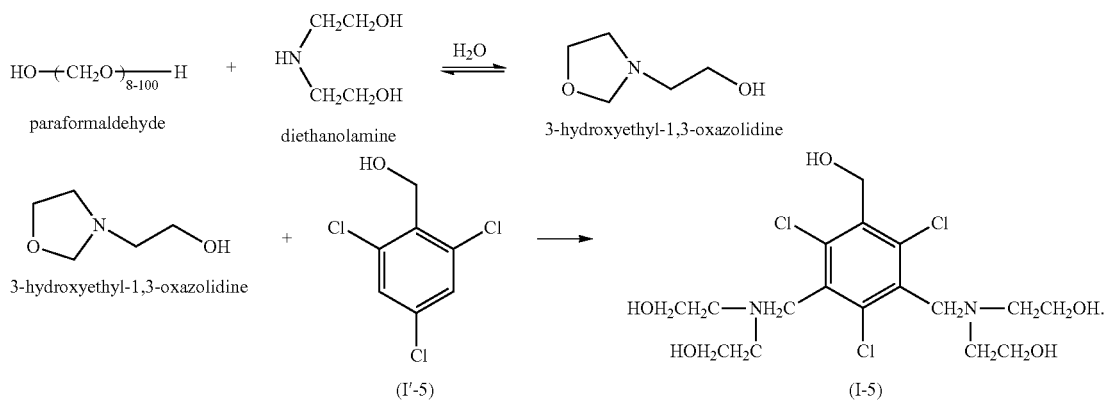

Embodiment 6

The present embodiment provides a Mannich base with a structure represented by a formula (I-6) as follows:

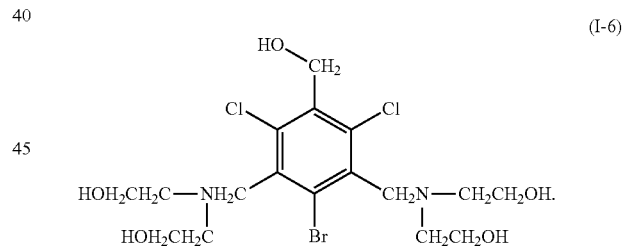

(I-6)

The Mannich base represented by the formula (I-6) is prepared through the following steps:

(1) adding 52.6 g of diethanolamine into a 250 mL round-bottomed flask, stirring, and heating up to a temperature of 40-45° C.; and then, adding 15 g of paraformaldehyde (molecular weight: 30) into the flask in four batches in a manner that the feeding time interval of each batch is 15 min and a temperature is controlled to be 50-60° C. during feeding of the paraformaldehyde;

After the paraformaldehyde is added completely, continuing to perform a reaction for a period of 3 h at a temperature of 50° C. to produce 3-hydroxyethyl-1,3-oxazolidine; and Heating up to a temperature of 100° C., and subjecting the produced 3-hydroxyethyl-1,3-oxazolidine to depressurized dewatering to enable the 3-hydroxyethyl-1,3-oxazolidine has a moisture content of equal to or less than 0.5%; and (2) cooling down to a temperature of 60-65° C., and adding 63.98 g of 2,6-dichloro-4-bromobenzalcohol (a phenyl compound represented by a formula (I'-6)) into the 3-hydroxyethyl-1,3-oxazolidine in 2 h in 3-4 batches; and after adding is completed, continuing to perform a reaction for a period of 3 h at a temperature of 80° C., thereby preparing the Mannich base represented by the formula (I-6).

A reaction route is shown as follows:

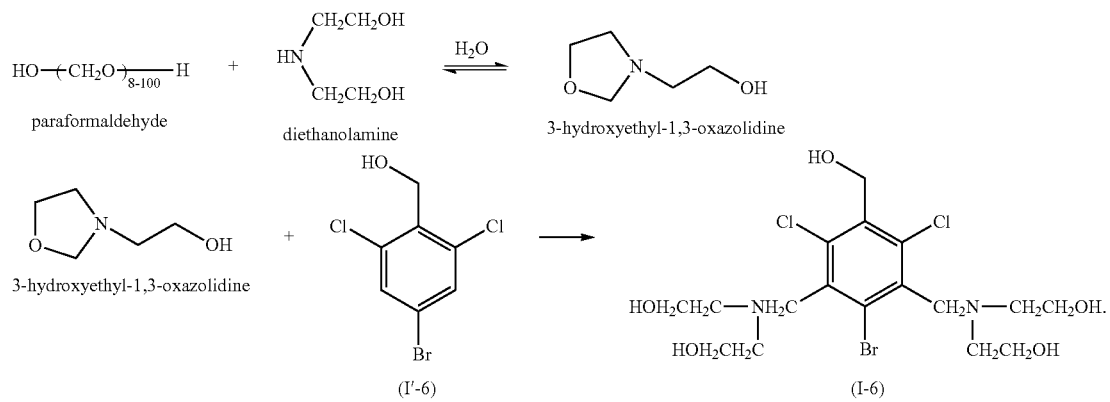

Embodiment 7

The present embodiment provides a Mannich base with a structure represented by a formula (I-7) as follows:

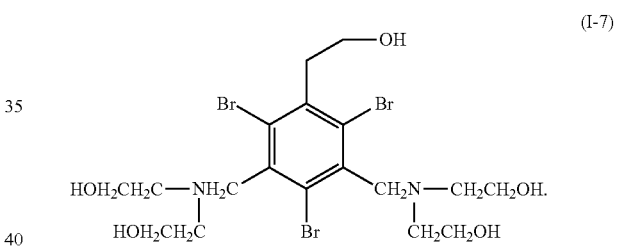

The Mannich base represented by the formula (I-7) is prepared through the following steps:

(1) adding 52.6 g of diethanolamine into a 250 mL round-bottomed flask, stirring, and heating up to a temperature of 40-45° C.; and then, adding 30 g of paraformaldehyde (molecular weight: 60) into the flask in four batches in a manner that the feeding time interval of each batch is 15 min and a temperature is controlled to be 50-58° C. during feeding of the paraformaldehyde;

After the paraformaldehyde is added completely, continuing to perform a reaction for a period of 3 h at a temperature of 58° C. to produce 3-hydroxyethyl-1,3-oxazolidine; and Heating up to a temperature of 100° C., and subjecting the produced 3-hydroxyethyl-1,3-oxazolidine to depressurized dewatering to enable the 3-hydroxyethyl-1,3-oxazolidine has a moisture content of equal to or less than 0.5%; and (2) cooling down to a temperature of 60-65° C., and adding 89.7 g of 2-(2,4,6-tribromophenyl)-ethanol (a phenyl compound represented by a formula (I'-7)) into the 3-hydroxyethyl-1,3-oxazolidine in 2 h in 3-4 batches; and after adding is completed, continuing to perform a reaction for a period of 2.5 h at a temperature of 80° C., thereby preparing the Mannich base represented by the formula (I-7).

A reaction route is shown as follows:

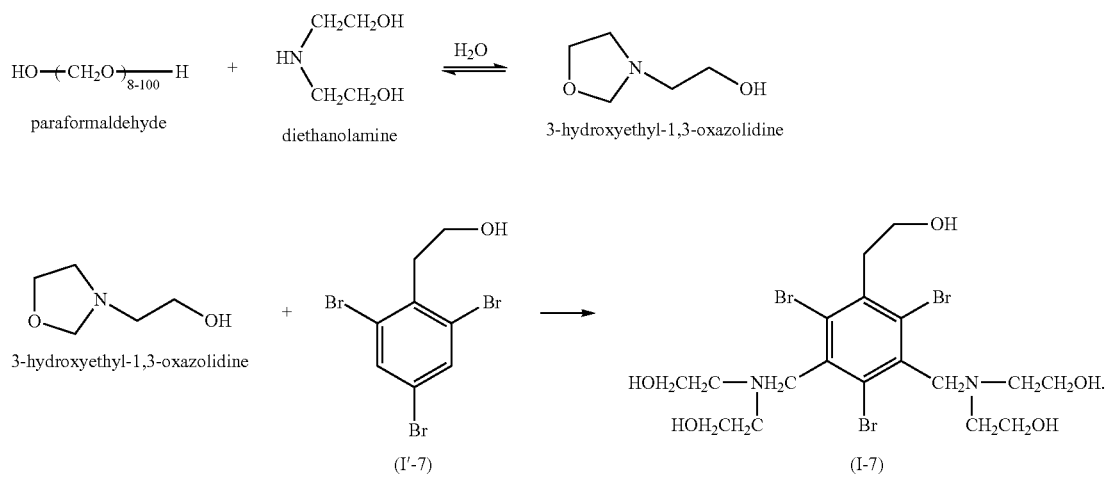

Embodiment 8

The present embodiment provides a Mannich base with a structure represented by a formula (I-8) as follows:

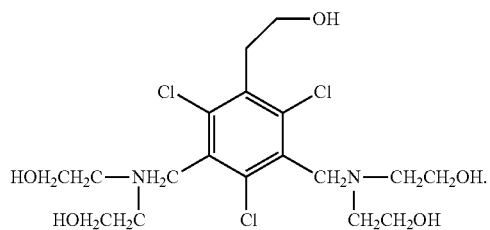

The Mannich base represented by the formula (I-8) is prepared through the following steps:

(1) adding 52.6 g of diethanolamine into a 250 mL round-bottomed flask, stirring, and heating up to a temperature of 40-45° C.; and then, adding 15 g of paraformaldehyde (molecular weight: 30) into the flask in four batches in a manner that the feeding time interval of each batch is 15 min and a temperature is controlled to be 54-58° C. during feeding of the paraformaldehyde;

After the paraformaldehyde is added completely, continuing to perform a reaction for a period of 3 h at a temperature of 55° C. to produce 3-hydroxyethyl-1,3-oxazolidine; and Heating up to a temperature of 100° C., and subjecting the produced 3-hydroxyethyl-1,3-oxazolidine to depressurized dewatering to enable the 3-hydroxyethyl-1,3-oxazolidine has a moisture content of equal to or less than 0.5%; and (2) cooling down to a temperature of 60-65° C., adding 56.4 g of 2-(2,4,6-trichlorophenyl)-ethanol (a phenyl compound represented by a formula (I'-8)) into the 3-hydroxyethyl-1,3-oxazolidine in 2 h in 3-4 batches; and after adding is completed, continuing to perform a reaction for a period of 2.5 h at a temperature of 83° C., thereby preparing the Mannich base represented by the formula (I-8).

A reaction route is shown as follows:

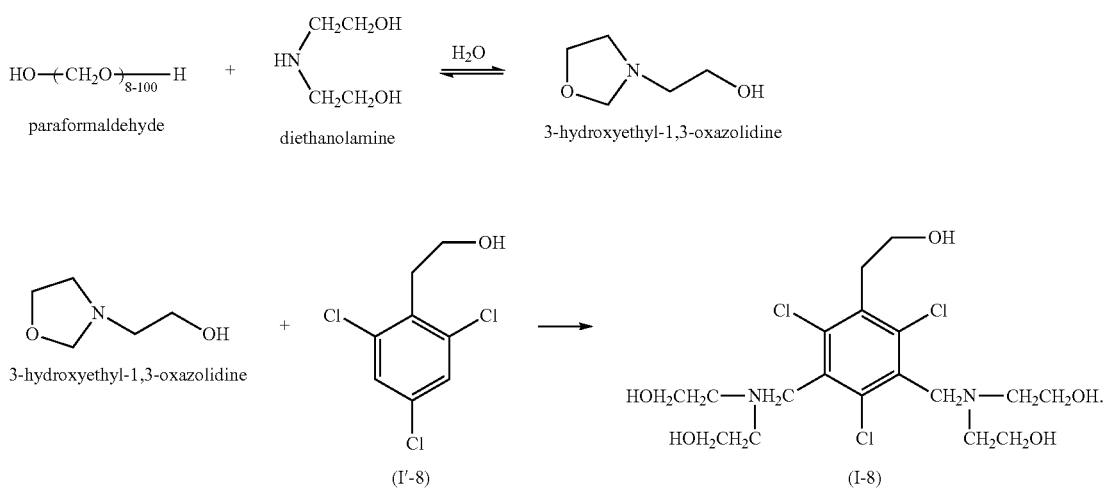

Embodiment 9

The present embodiment provides a flame-retardant polyether polyol. The flame-retardant polyether polyol is synthesized from raw materials including a Mannich base and ethylene oxide, wherein the Mannich base has a structure represented by a formula (I-1):

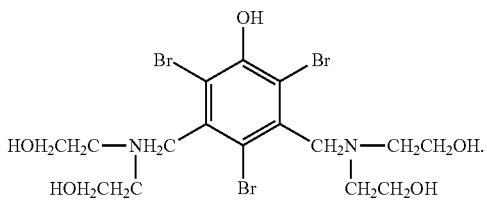

(I-1)

A preparation method of the flame-retardant polyether polyol includes the following steps:

(1) adding 11.2 g of the Mannich base with a structure represented by the formula (I-1) into an autoclave, performing vacuumizing and nitrogen gas replacement for 3 times, adding a catalyst KOH, and stirring uniformly; and heating up a temperature in the autoclave to 80° C., then, introducing ethylene oxide while controlling a pressure to be 0.2 MPa and controlling a temperature to be 103±2° C., and closing the ethylene oxide in 0.5 h~1 h;

(2) after the introducing of the ethylene oxide is completed, continuing to control the temperature in the autoclave to be 85° C., stirring for a period of 1 h, and subjecting the Mannich base with the structure represented by the formula (I-1) and the ethylene oxide to a reaction to produce a precursor of the flame-retardant polyether polyol; and (3) subjecting the precursor of the flame-retardant polyether polyol obtained in the step (2) to vacuum dewatering for a period of 0.5 h at a temperature of 90° C., cooling down, and adding glacial acetic acid for neutralization, thereby obtaining the flame-retardant polyether polyol with a hydroxyl value of 470~490 mgKOH/g and a viscosity of 10000~15000.

Embodiment 10

The present embodiment provides a flame-retardant polyether polyol. The flame-retardant polyether polyol is synthesized from raw materials including a Mannich base and propylene oxide, wherein the Mannich base has a structure represented by a formula (I-2):

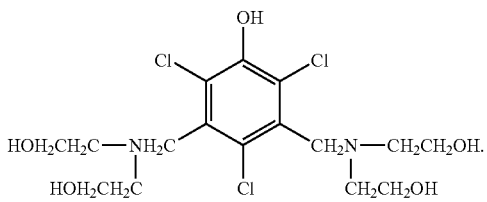

(I-2)

A preparation method of the flame-retardant polyether polyol includes the following steps:

(1) adding 10 g of the Mannich base with a structure represented by the formula (I-2) into an autoclave, performing vacuumizing and nitrogen gas replacement for 3 times, adding a catalyst KOH, and stirring uniformly; heating up a temperature in the autoclave to 85° C., then, introducing ethylene oxide while controlling a pressure to be 0.2 MPa and controlling a temperature to be 103±2° C., and closing the ethylene oxide in 0.5 h; and introducing propylene oxide while controlling a pressure to be 0.2 MPa and controlling a temperature to be 103±2° C., and closing the propylene oxide in 0.5 h;

(2) after the introducing of a mixed monomer is completed, continuing to control the temperature in the autoclave to be 100° C., stirring for a period of 1 h, and subjecting the Mannich base with the structure represented by the formula (I-2) and the propylene oxide to a reaction to produce a precursor of the flame-retardant polyether polyol; and (3) subjecting the precursor of the flame-retardant polyether polyol obtained in the step (2) to vacuum dewatering for a period of 0.5 h at a temperature of 100° C., cooling down, and adding glacial acetic acid for neutralization, thereby obtaining the flame-retardant polyether polyol with a hydroxyl value of 430~470 mgKOH/g and a viscosity of 10000~15000.

Embodiment 11

The present embodiment provides a flame-retardant polyether polyol. The flame-retardant polyether polyol is synthesized from raw materials including a Mannich base and ethylene oxide, wherein the Mannich base has a structure represented by a formula (I-3):

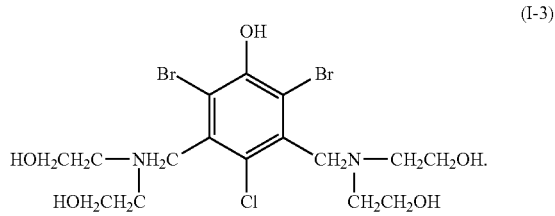

(I-3)

A preparation method of the flame-retardant polyether polyol includes the following steps:

(1) adding 11 g of the Mannich base with a structure represented by the formula (I-3) into an autoclave, performing vacuumizing and nitrogen gas replacement for 3 times, adding a catalyst KOH, and stirring uniformly; and heating up a temperature in the autoclave to 80° C., then, introducing ethylene oxide while controlling a pressure to be 0.2 MPa and controlling a temperature to be 103±2° C., and closing the ethylene oxide in 0.5 h~1 h;

(2) after the introducing of the ethylene oxide is completed, continuing to control the temperature in the autoclave to be 85° C., stirring for a period of 1.5 h, and subjecting the Mannich base with the structure represented by the formula (I-3) and the ethylene oxide to a reaction to produce a precursor of the flame-retardant polyether polyol; and (3) subjecting the precursor of the flame-retardant polyether polyol obtained in the step (2) to vacuum dewatering for a period of 1 h at a temperature of 90° C., cooling down, and adding glacial acetic acid for neutralization, thereby obtaining the flame-retardant polyether polyol with a hydroxyl value of 450~480 mgKOH/g and a viscosity of 10000~15000.

Embodiment 12

The present embodiment provides a flame-retardant polyether polyol. The flame-retardant polyether polyol is synthesized from raw materials including a Mannich base and ethylene oxide, wherein the Mannich base has a structure represented by a formula (I-4):

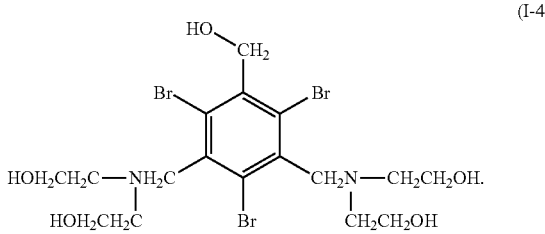

(I-4)

A preparation method of the flame-retardant polyether polyol includes the following steps:

(1) adding 12 g of the Mannich base with a structure represented by the formula (I-4) into an autoclave, performing vacuumizing and nitrogen gas replacement for 3 times, adding a catalyst KOH, and stirring uniformly; and heating up a temperature in the autoclave to 85° C., then, introducing ethylene oxide while controlling a pressure to be 0.2 MPa and controlling a temperature to be 103±2° C., and closing the ethylene oxide in 0.5 h~1 h;

(2) after the introducing of the ethylene oxide is completed, continuing to control the temperature in the autoclave to be 95° C., stirring for a period of 1.5 h, and subjecting the Mannich base with the structure represented by the formula (I-4) and the ethylene oxide to a reaction to produce a precursor of the flame-retardant polyether polyol; and (3) subjecting the precursor of the flame-retardant polyether polyol obtained in the step (2) to vacuum dewatering for a period of 0.8 h at a temperature of 95° C., cooling down, and adding glacial acetic acid for neutralization, thereby obtaining the flame-retardant polyether polyol with a hydroxyl value of 450~480 mgKOH/g and a viscosity of 10000~15000.

Embodiment 13

The present embodiment provides a flame-retardant polyether polyol. The flame-retardant polyether polyol is synthesized from raw materials including a Mannich base and ethylene oxide, wherein the Mannich base has a structure represented by a formula (I-5):

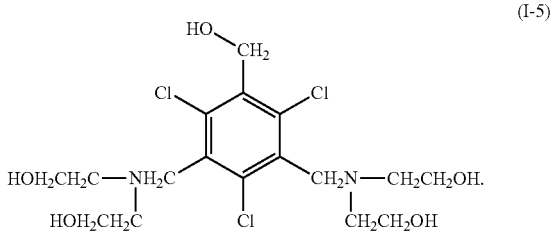

(I-5)

A preparation method of the flame-retardant polyether polyol includes the following steps:

(1) adding 11 g of the Mannich base with a structure represented by the formula (I-5) into an autoclave, performing vacuumizing and nitrogen gas replacement for 3 times, adding a catalyst KOH, and stirring uniformly; and heating up a temperature in the autoclave to 80° C., then, introducing ethylene oxide while controlling a pressure to be 0.2 MPa and controlling a temperature to be 103±2° C., and closing the ethylene oxide in 0.5 h~1 h;

(2) after the introducing of the ethylene oxide is completed, continuing to control the temperature in the autoclave to be 100° C., stirring for a period of 1 h, and subjecting the Mannich base with the structure represented by the formula (I-5) and the ethylene oxide to a reaction to produce a precursor of the flame-retardant polyether polyol; and (3) subjecting the precursor of the flame-retardant polyether polyol obtained in the step (2) to vacuum dewatering for a period of 1 h at a temperature of 90° C., cooling down, and adding glacial acetic acid for neutralization, thereby obtaining the flame-retardant polyether polyol with a hydroxyl value of 450~480 mgKOH/g and a viscosity of 10000~15000.

Embodiment 14

The present embodiment provides a flame-retardant polyether polyol. The flame-retardant polyether polyol is synthesized from raw materials including a Mannich base and propylene oxide, wherein the Mannich base has a structure represented by a formula (I-6):

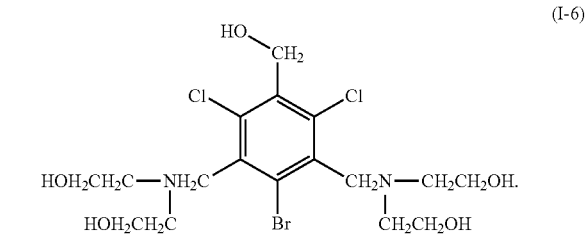

(I-6)

A preparation method of the flame-retardant polyether polyol includes the following steps:

(1) adding 11.5 g of the Mannich base with a structure represented by the formula (I-6) into an autoclave, performing vacuumizing and nitrogen gas replacement for 3 times, adding a catalyst KOH, and stirring uniformly; and heating up a temperature in the autoclave to 80° C., then, introducing propylene oxide while controlling a pressure to be 0.2 MPa and controlling a temperature to be 103±2° C., and closing the propylene oxide in 0.5 h~1 h;

(2) after the introducing of the propylene oxide is completed, continuing to control the temperature in the autoclave to be 85° C., stirring for a period of 1.5 h, and subjecting the Mannich base with the structure represented by the formula (I-6) and the propylene oxide to a reaction to produce a precursor of the flame-retardant polyether polyol; and (3) subjecting the precursor of the flame-retardant polyether polyol obtained in the step (2) to vacuum dewatering for a period of 0.5 h at a temperature of 100° C., cooling down, and adding glacial acetic acid for neutralization, thereby obtaining the flame-retardant polyether polyol with a hydroxyl value of 460~485 mgKOH/g and a viscosity of 10000~15000.

Embodiment 15

The present embodiment provides a flame-retardant polyether polyol. The flame-retardant polyether polyol is synthesized from raw materials including a Mannich base and ethylene oxide, wherein the Mannich base has a structure represented by a formula (I-7):

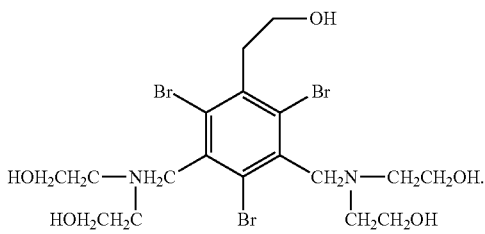

(I-7)

A preparation method of the flame-retardant polyether polyol includes the following steps:

(1) adding 13 g of the Mannich base with a structure represented by the formula (I-7) into an autoclave, performing vacuumizing and nitrogen gas replacement for 3 times, adding a catalyst KOH, and stirring uniformly; and heating up a temperature in the autoclave to 80° C., then, introducing ethylene oxide while controlling a pressure to be 0.2 MPa and controlling a temperature to be 103±2° C., and closing the ethylene oxide in 0.5 h~1 h;

(2) after the introducing of the ethylene oxide is completed, continuing to control the temperature in the autoclave to be 85° C., stirring for a period of 1 h, and subjecting the Mannich base with the structure represented by the formula (I-7) and the ethylene oxide to a reaction to produce a precursor of the flame-retardant polyether polyol; and (3) subjecting the precursor of the flame-retardant polyether polyol obtained in the step (2) to vacuum dewatering for a period of 0.5 h at a temperature of 90° C., cooling down, and adding glacial acetic acid for neutralization, thereby obtaining the flame-retardant polyether polyol with a hydroxyl value of 460~490 mgKOH/g and a viscosity of 10000~15000.

Embodiment 16

The present embodiment provides a flame-retardant polyether polyol. The flame-retardant polyether polyol is synthesized from raw materials including a Mannich base and ethylene oxide, wherein the Mannich base has a structure represented by a formula (I-8):

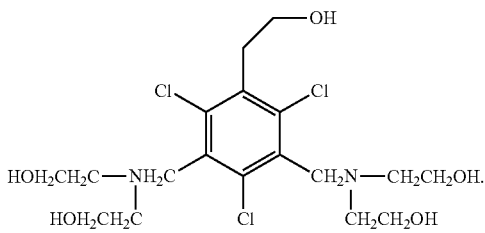

(I-8)

A preparation method of the flame-retardant polyether polyol includes the following steps:

(1) adding 12 g of the Mannich base with a structure represented by the formula (I-8) into an autoclave, performing vacuumizing and nitrogen gas replacement for 3 times, adding a catalyst KOH, and stirring uniformly; and heating up a temperature in the autoclave to 80° C., then, introducing ethylene oxide while controlling a pressure to be 0.2 MPa and controlling a temperature to be 103±2° C., and closing the ethylene oxide in 0.5 h~1 h;

(2) after the introducing of the ethylene oxide is completed, continuing to control the temperature in the autoclave to be 85° C., stirring for a period of 1 h, and subjecting the Mannich base with the structure represented by the formula (I-8) and the ethylene oxide to a reaction to produce a precursor of the flame-retardant polyether polyol; and (3) subjecting the precursor of the flame-retardant polyether polyol obtained in the step (2) to vacuum dewatering for a period of 0.5 h at a temperature of 90° C., cooling down, and adding glacial acetic acid for neutralization, thereby obtaining the flame-retardant polyether polyol with a hydroxyl value of 470~495 mgKOH/g and a viscosity of 10000~15000.

Embodiment 17

The present embodiment provides a flame-retardant polyurethane material. In parts by mass, a component A of raw materials for synthesizing the flame-retardant polyurethane material includes:

70 parts of the flame-retardant polyether polyol prepared in the embodiment 9, 30 parts of polyether polyol taking saccharose as an initiator, 2.5 parts of a foam stabilizer, 2 parts of water, 20 parts of a foamer and 1.5 parts of a catalyst (N,N-dimethylbenzylamine); and A component B includes 126 parts of isocyanate.

The flame-retardant polyurethane material is prepared through the following method:

Weighing a certain amount of the component A, and placing the component A in a plastic cup; and weighing an isocyanate as the component B according to a raw material proportioning ratio, and placing the component B in another plastic cup. Rapidly pouring the component B into just-uniformly-stirred component A, continuing to rapidly stir for a period of 5-10 s, recording the reaction time, aging for a period of 24 h at normal temperature, and testing properties.

Embodiment 18

The present embodiment provides a flame-retardant polyurethane material. In parts by mass, a component A of raw materials for synthesizing the flame-retardant polyurethane material includes:

60 parts of the flame-retardant polyether polyol prepared in the embodiment 10, 40 parts of polyether polyol taking saccharose as an initiator, 1.5 parts of a foam stabilizer, 2 parts of water, 25 parts of a foamer and 1.5 parts of a catalyst (N,N-dimethylcyclohexylamine); and A component B includes 130 parts of isocyanate.

A preparation method of the flame-retardant polyurethane material is the same as that in the embodiment 17.

Embodiment 19

The present embodiment provides a flame-retardant polyurethane material. In parts by mass, a component A of raw materials for synthesizing the flame-retardant polyurethane material includes:

30 parts of the flame-retardant polyether polyol prepared in the embodiment 11, 70 parts of polyether polyol taking sorbitol as an initiator, 2.0 parts of a foam stabilizer, 2 parts of water, 20 parts of a foamer and 1.5 parts of a catalyst (N,N'-dimethylpyridine); and A component B includes 125.5 parts of isocyanate.

A preparation method of the flame-retardant polyurethane material is the same as that in the embodiment 17.

Embodiment 20

The present embodiment provides a flame-retardant polyurethane material. In parts by mass, a component A of raw materials for synthesizing the flame-retardant polyurethane material includes:

15 parts of the flame-retardant polyether polyol prepared in the embodiment 12, 85 parts of polyether polyol taking sorbitol as an initiator, 2 parts of a foam stabilizer, 2 parts of water, 25 parts of a foamer and 1.5 parts of a catalyst (N,N-dimethylbenzylamine); and A component B includes 130.5 parts of isocyanate.

A preparation method of the flame-retardant polyurethane material is the same as that in the embodiment 17.

Embodiment 21

The present embodiment provides a flame-retardant polyurethane material. In parts by mass, a component A of raw materials for synthesizing the flame-retardant polyurethane material includes:

70 parts of the flame-retardant polyether polyol prepared in the embodiment 13, 30 parts of polyether polyol taking sorbitol as an initiator, 1.5 parts of a foam stabilizer, 2 parts of water, 25 parts of a foamer and 1.5 parts of a catalyst (N,N-dimethylcyclohexylamine); and A component B includes 130 parts of isocyanate.

A preparation method of the flame-retardant polyurethane material is the same as that in the embodiment 17.

Embodiment 22

The present embodiment provides a flame-retardant polyurethane material. In parts by mass, a component A of raw materials for synthesizing the flame-retardant polyurethane material includes:

30 parts of the flame-retardant polyether polyol prepared in the embodiment 14, 70 parts of polyether polyol taking saccharose as an initiator, 2.0 parts of a foam stabilizer, 2 parts of water, 20 parts of a foamer and 1.5 parts of a catalyst (N,N-dimethylcyclohexylamine); and A component B includes 125.5 parts of isocyanate.

A preparation method of the flame-retardant polyurethane material is the same as that in the embodiment 17.

Embodiment 23

The present embodiment provides a flame-retardant polyurethane material. In parts by mass, a component A of raw materials for synthesizing the flame-retardant polyurethane material includes:

70 parts of the flame-retardant polyether polyol prepared in the embodiment 15, 30 parts of polyether polyol taking saccharose as an initiator, 1.5 parts of a foam stabilizer, 2 parts of water, 20 parts of a foamer and 1.5 parts of a catalyst (N,N-dimethylbenzylamine); and A component B includes 125 parts of isocyanate.

A preparation method of the flame-retardant polyurethane material is the same as that in the embodiment 17.

Embodiment 24

The present embodiment provides a flame-retardant polyurethane material. In parts by mass, a component A of raw materials for synthesizing the flame-retardant polyurethane material includes:

30 parts of the flame-retardant polyether polyol prepared in the embodiment 16, 60 parts of polyether polyol taking saccharose as an initiator, 2.5 parts of a foam stabilizer, 2 parts of water, 25 parts of a foamer and 2 parts of a catalyst (N,N-dimethylbenzylamine); and A component B includes 131.5 parts of isocyanate.

A preparation method of the flame-retardant polyurethane material is the same as that in the embodiment 17.

Embodiment 25

The present embodiment provides a polyurethane material. In parts by mass, a component A of raw materials for synthesizing the polyurethane material includes:

100 parts of polyether polyol taking saccharose as an initiator, 2.5 parts of a foam stabilizer, 2 parts of water, 20 parts of a foamer and 2 parts of a catalyst (N,N'-dimethylpyridine); and A component B includes 126.5 parts of isocyanate.

A preparation method of the polyurethane material is the same as that in the embodiment 17.

Experimental Example 1

Testing on product performance of the polyurethane materials of the embodiments 17-25: apparent density of the flame-retardant polyurethane materials is assayed according to GB 6343-1986; an oxygen index is assayed according to GB/T 2406-1993; compression strength is tested according to GB 8813-1988, dimensional stability of rigid foam is tested at low temperature according to GB/T 8811-1988, and test results are shown in a table 1.

TABLE 1

Test on product performance of flame-retardant polyurethane materials

| Flame-retardant polyurethane materials | Cream time/s | Gel time/s | Non-sticky time/s | Density/ Kg/m$^3$ | Compression strength (deformation 10%)/kPa | Dimensional stability (70° C., 48 h)/% | Oxygen index | Flame-retardant Rating |
|---|---|---|---|---|---|---|---|---|
| Embodiment 17 | 9 | 41 | 79 | 25 | 150 | <1.0 | 32 | B$_1$ |
| Embodiment 18 | 12 | 46 | 84 | 27 | 162 | <1.0 | 29 | B$_1$ |
| Embodiment 19 | 14 | 47 | 86 | 28 | 165 | <1.0 | 26 | B$_2$ |
| Embodiment 20 | 19 | 53 | 90 | 31 | 170 | <1.0 | 24 | B$_2$ |

TABLE 1-continued

Test on product performance of flame-retardant polyurethane materials

| Flame-retardant polyurethane materials | Cream time/s | Gel time/s | Non-sticky time/s | Density/ Kg/m$^3$ | Compression strength (deformation 10%)/kPa | Dimensional stability (70° C., 48 h)/% | Oxygen index | Flame-retardant Rating |
|---|---|---|---|---|---|---|---|---|
| Embodiment 21 | 8 | 41 | 74 | 26 | 157 | <1.0 | 32 | B$_1$ |
| Embodiment 22 | 20 | 64 | 103 | 31 | 172 | <1.0 | 25 | B$_2$ |
| Embodiment 23 | 9 | 42 | 76 | 26 | 160 | <1.0 | 32 | B$_1$ |
| Embodiment 24 | 13 | 45 | 82 | 27 | 162 | <1.0 | 25 | B$_2$ |
| Embodiment 25 | 24 | 74 | 117 | 31 | 140 | <1.0 | 21 | B$_3$ |

Known from the above table 1, the flame-retardant polyurethane materials prepared in the embodiments 17-24 of the present disclosure have high compression strength, dimensional stability and oxygen indexes, flame-retardant ratings thereof are high, and the time required for emulsification and gelatination is short. It is indicated that flame retardance of polyurethane materials synthesized by using the flame-retardant polyether polyol provided by the present disclosure is effectively improved, and the materials are accompanied with high mechanical properties; and known from the table 1, after a use proportion of the flame-retardant polyether polyol is increased, reactivity of a system can be obviously improved, and flame retardance of the prepared flame-retardant polyurethane materials is also further improved.

Apparently, the above-mentioned embodiments are only intended for clearly describing made examples, rather than defining embodiments. For those having ordinary skill in the art, changes or variations of other different forms can also be made on the basis of the above-mentioned description. Herein, all embodiments are not required to and cannot be exhaustive. Readily apparent changes or variations evolved therefrom still fall within the protection scope of the present disclosure.

The invention claimed is:

1. A method for preparing a flame-retardant polyurethane material, comprising preparing a polyether polyol from a Mannich base, and preparing a flame-retardant polyurethane material from the polyether polyol, wherein the Mannich base has a structure represented by a formula (I):

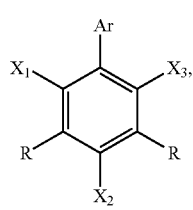

wherein, Ar is hydroxyl or hydroxyl substituted C1~C16 alkyl, R is

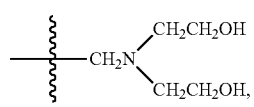

and X$_1$, X$_2$ and X$_3$, independently of each other, represent a halogen, wherein the Mannich base is prepared by a method comprising the following steps:

(1) performing a reaction by heating diethanolamine, then adding paraformaldehyde into the diethanolamine in batches, and controlling a temperature of 50-60° C., producing 3-hydroxyethyl-1,3-oxazolidine; and (2) performing a reaction by adding a phenyl compound into the 3-hydroxyethyl-1,3-oxazolidine, producing the Mannich base with a structure represented by the formula (I);

wherein the phenyl compound has a structure represented by a formula (I') as follows:

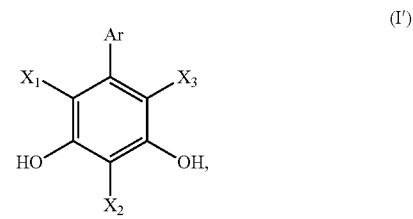

wherein, Ar is hydroxyl or hydroxyl substituted C1~C16 alkyl and X$_1$, X$_2$ and X$_3$, independently of each other, represent a halogen.

2. The method according to claim 1, wherein in the step (2), the 3-hydroxyethyl-1,3-oxazolidine is reacted with the phenyl compound at a temperature of 80-85° C. for a period of 2.5-3h.

3. The method according to claim 1, wherein a mole ratio of the diethanolamine to the paraformaldehyde to the phenyl compound is (2-2.15):(2-2.1):1.

4. The method according to claim 1, wherein the paraformaldehyde is added in 4 batches within a period of not exceeding 40 minutes under a temperature of 50-60° C.

5. The method according to claim 1, wherein the phenyl compound is added in 3-4 batches within a period of not exceeding 2 hours.

6. The method according to claim 1, comprising preparing a polyether polyol by copolymerization of the Mannich base and an epoxide, and then preparing a flame-retardant polyurethane material by reacting the polyether polyol with an isocyanate.

7. The method according to claim 6, wherein the epoxide is one or more selected from the group consisting of ethylene oxide, propylene oxide and butylene oxide.

8. The method according to claim 6, wherein a mole ratio of the Mannich base to the epoxide is 1:(1-200).

9. The method according to claim 6, wherein said preparing a flame-retardant polyurethane material comprises reacting 30-70 parts by mass of the polyether polyol with 125-131.5 parts by mass of the isocyanate.

10. The method according to claim 1, wherein $X_1$, $X_2$ and $X_3$, independently of each other, represent bromo or chloro.

11. The method according to claim 1, wherein the Mannich base has a structure represented by a formula (II):

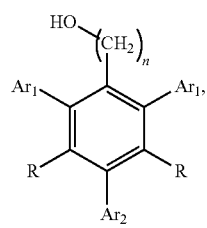

(II)

wherein, n is an integer of 1-16, R is

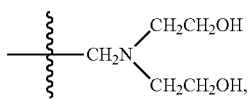

and $Ar_1$ and $Ar_2$, independently of each other, represent bromo or chloro.

12. The method according to claim 1, wherein the Mannich base has a structure represented by any of the following formulae (I-1)-(I-12):

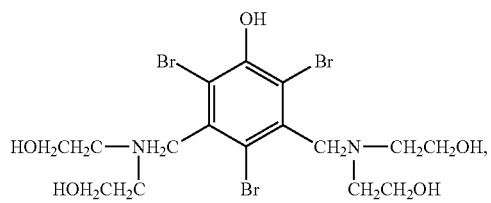

(I-1)

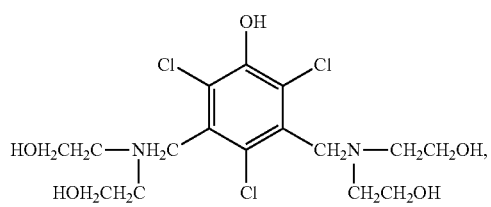

(I-2)

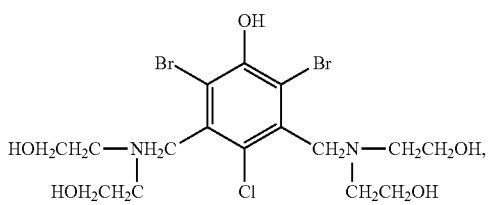

(I-3)

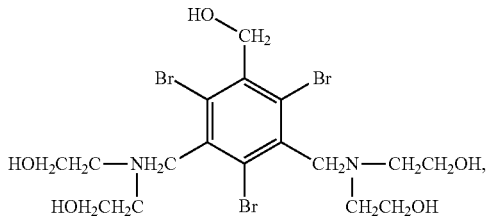

(I-4)

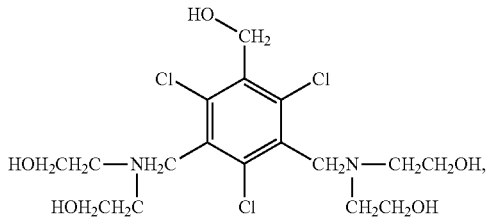

(I-5)

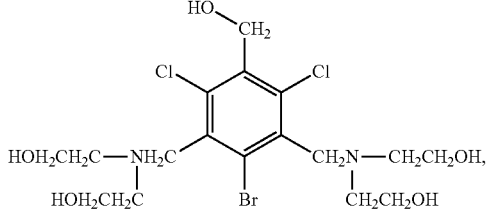

(I-6)

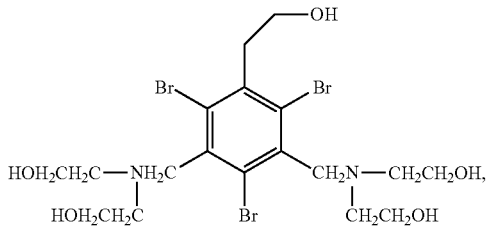

(I-7)

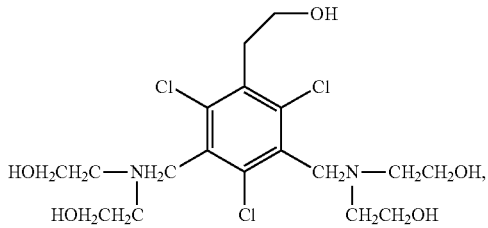

(I-8)

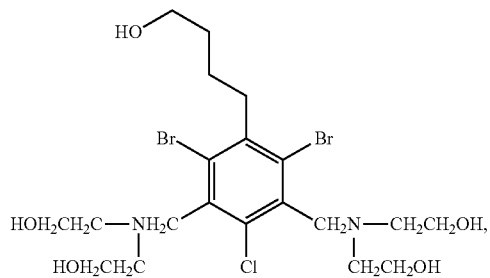
(I-9)
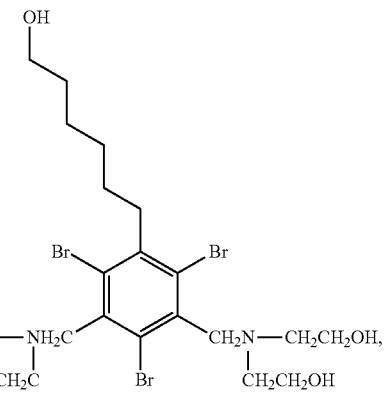
(I-11)
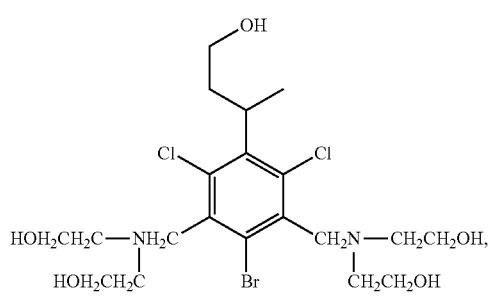
(I-10)
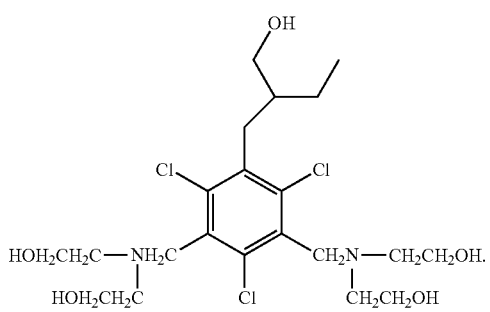
(I-12)
* * * * *